(12) United States Patent
Arlinghaus, Jr.

(10) Patent No.: US 10,532,171 B2
(45) Date of Patent: Jan. 14, 2020

(54) TRACHEOSTOMY OR ENDOTRACHEAL TUBE ADAPTER FOR SPEECH

(71) Applicant: Frank H. Arlinghaus, Jr., Rumson, NJ (US)

(72) Inventor: Frank H. Arlinghaus, Jr., Rumson, NJ (US)

(73) Assignee: Frank H. Arlinghaus, Jr., Rumson, NJ (US)

( * ) Notice: Subject to any disclaimer, the term of this patent is extended or adjusted under 35 U.S.C. 154(b) by 111 days.

(21) Appl. No.: 15/119,225

(22) PCT Filed: Sep. 4, 2015

(86) PCT No.: PCT/US2015/048574
§ 371 (c)(1),
(2) Date: Aug. 16, 2016

(87) PCT Pub. No.: WO2016/053574
PCT Pub. Date: Apr. 7, 2016

(65) Prior Publication Data
US 2017/0203066 A1    Jul. 20, 2017

Related U.S. Application Data

(60) Provisional application No. 62/057,326, filed on Sep. 30, 2014.

(51) Int. Cl.
*A61M 16/04*  (2006.01)
*A61F 2/20*  (2006.01)
(Continued)

(52) U.S. Cl.
CPC ......... *A61M 16/0468* (2013.01); *A61B 1/267* (2013.01); *A61F 2/20* (2013.01);
(Continued)

(58) Field of Classification Search
CPC ..... A61B 1/267; A61B 5/0421; A61B 5/0488; A61B 5/0536; A61B 5/082; A61B 5/4052;
(Continued)

(56) References Cited

U.S. PATENT DOCUMENTS 3,683,931 A * 8/1972 Chelucci ............ A61M 16/0468
128/207.16
4,240,417 A * 12/1980 Holever ............ A61M 16/0465
128/203.12
(Continued)

FOREIGN PATENT DOCUMENTS

JP  2012/055472 A   3/2012
WO  90/14854   12/1990

OTHER PUBLICATIONS

Passy-Muir® Valves, Accessories, & Connections Guide, http://www.passy-muir.com/sites/default/files/pdf/connectaccessguide.pdf.
(Continued)

*Primary Examiner* — Annette Dixon
(74) *Attorney, Agent, or Firm* — Hoffmann & Baron LLP (57) ABSTRACT

A speaking valve adapter is disclosed for assisting with speech or language expression during the respiratory recovery of a human. The speaking valve adapter including a speaking valve port, the port being orthogonal to a first interface port, the first interface port adapted to support tracheostomy or endotracheal tubing, a second interface port adapted to support at least one of a suction tubing and a bronchoscopy tubing, and a third interface port adapted to support a connection to a ventilator. The speaking valve adapter may be used by the patient for introduction of at least one of sounds and words while connected to the ventilator. A corresponding respiratory management system which implements the speaking valve adapter and configurable ventilator settings adapted for assisting with more (Continued)

effective speech or language expression during patient recovery or use is also disclosed.

22 Claims, 9 Drawing Sheets (51) Int. Cl.

| | | |
|---|---|---|
| *A61M 16/08* | (2006.01) | |
| *A61B 1/267* | (2006.01) | |
| *A61M 16/00* | (2006.01) | |
| *A61B 5/00* | (2006.01) | |
| *A61J 15/00* | (2006.01) | |
| *A61B 5/042* | (2006.01) | |
| *A61B 5/0488* | (2006.01) | |
| *A61B 5/053* | (2006.01) | |
| *A61B 5/08* | (2006.01) | |

(52) U.S. Cl.
CPC ...... *A61M 16/0051* (2013.01); *A61M 16/021* (2017.08); *A61M 16/0434* (2013.01); *A61M 16/0463* (2013.01); *A61M 16/0816* (2013.01); *A61B 5/0421* (2013.01); *A61B 5/0488* (2013.01); *A61B 5/0536* (2013.01); *A61B 5/082* (2013.01); *A61B 5/4052* (2013.01); *A61B 5/6865* (2013.01); *A61F 2002/206* (2013.01); *A61J 15/0003* (2013.01); *A61J 15/0084* (2015.05); *A61M 2230/60* (2013.01)

(58) Field of Classification Search
CPC .......... A61B 5/6865; A61F 2/20; A61F 2/203; A61F 2002/206; A61J 15/0003; A61J 15/0084; A61M 16/0051; A61M 16/021; A61M 16/04; A61M 16/0434; A61M 16/044; A61M 16/0461; A61M 16/0463; A61M 16/0468; A61M 16/0486; A61M 16/0816; A61M 16/208; A61M 2210/0618; A61M 2230/005; A61M 2230/60; Y10S 128/911

USPC ....... 128/207.15, 207.16, 207.18, 911; 623/9
See application file for complete search history.

(56) References Cited

U.S. PATENT DOCUMENTS

| | | | |
|---|---|---|---|
| 4,351,328 | A | 9/1982 | Bodai |
| 4,573,460 | A | 3/1986 | Szachowicz et al. |
| 4,774,945 | A | 10/1988 | White et al. |
| 5,259,378 | A | 11/1993 | Huchon et al. |
| 5,322,073 | A * | 6/1994 | Michels ............... A61J 15/0026 128/869 |
| 5,355,876 | A | 10/1994 | Brodsky et al. |
| 5,735,271 | A * | 4/1998 | Lorenzen .......... A61M 16/0463 128/200.26 |
| 5,738,091 | A | 4/1998 | Kee et al. |
| 5,806,515 | A | 9/1998 | Bare et al. |
| 6,334,441 | B1 | 1/2002 | Zowtiak et al. |
| 6,543,449 | B1 * | 4/2003 | Woodring ......... A61M 16/0051 128/204.18 |
| 6,612,304 | B1 | 9/2003 | Cise et al. |
| 6,978,783 | B2 | 12/2005 | Svendsen |
| 7,210,476 | B2 | 5/2007 | Blomquist |
| 7,556,041 | B2 * | 7/2009 | Madsen ............ A61M 16/0463 128/200.26 |
| 7,997,272 | B2 | 8/2011 | Isaza |
| 8,677,999 | B2 | 3/2014 | Allum et al. |
| 2005/0126578 | A1* | 6/2005 | Garrison ............... A61H 9/0078 128/874 |
| 2012/0145156 | A1 | 6/2012 | Lofaso et al. |
| 2013/0025591 | A1 | 1/2013 | Clark et al. |
| 2014/0238398 | A1 | 8/2014 | Christopher et al. |

OTHER PUBLICATIONS

Hess, Dean R., "Facilitating Speech in the Patient With a Tracheostomy", Respiratory Care, Apr. 2005, vol. 50, No. 4, pp. 519-525.

* cited by examiner

TRACHEOSTOMY OR ENDOTRACHEAL TUBE ADAPTER FOR SPEECH

CROSS REFERENCE TO RELATED APPLICATIONS

This application claims priority to International Application No. PCT/US2015/048574 filed on Sep. 4, 2015, which claims the benefit of priority of U.S. Provisional Patent Application No. 62/057,326 filed on Sep. 30, 2014, both of which are incorporated by reference herein in its their entirety for all purposes.

FIELD OF THE DISCLOSURE

The present disclosure relates to a speaking valve adapter implemented with a breathing apparatus or ventilator and related system, and more particularly, to a ventilator tracheostomy or endotracheal tube adapter for speech that may be implemented with current ventilator technologies. The disclosure permits the implementation of the improved features available in current ventilator technologies while permitting the patient to rehabilitate their lungs and/or respiratory airways during their recovery more effectively.

BACKGROUND

Speaking valves are generally utilized for patients that require a tracheostomy for breathing. In certain cases, patients are recovering from a debilitating lung injury or from a serious respiratory illness such as pneumonia that requires the patient's dependency on a ventilator for breathing during the recovery period or for an indefinite period of time. Other patients, such as quadriplegics may require a ventilator for breathing on a permanent basis. Tracheostomies are generally known to result in fewer complications for patients and generally recommended early on during treatment and recovery.

Tracheostomies are utilized via an opening surgically created through the neck into the trachea permitting access for breathing and is commonly done in an operating room under general anesthesia. A tube is usually placed through this opening to provide an airway and to remove secretions from the lungs. Thus, breathing or ventilation is accomplished through the tracheostomy tube rather than through the nose and mouth. The incision into the trachea (windpipe) forms a temporary or permanent opening which connects via the tracheostomy tube to a ventilator so the patient can safely recover while maintaining respiration.

However, one of the problems faced by patients that require a tracheostomy tube is that speaking often becomes a challenge. Exhaled air generally does not pass through their larynx but, rather exits from the tracheostomy tube. A speaking valve is often attached to the tracheostomy tube to direct air flow through the vocal cords when a patient exhales. The speaking valve thus closes during exhalation, causing air to travel up the trachea around the tracheostomy tube, through the larynx and out of the patient's nose or mouth. This re-directed air path permits speech in the patient.

While speaking valves have been implemented to assist the patient with speaking, the use of such valves includes various drawbacks. Some of the concerns with one-way speaking valves have included occlusion problems, safety, high resistance levels, size, adaptability, restriction during inspiration, and leakage of exhaled air backing out through the valve.

Many speaking valves are designed in a biased-closed position that open only during inspiration and start to close before the end of the inspiratory cycle/beginning of the expiratory cycle. The air is then directed around the tracheostomy tube, through the vocal cords and out through the oral and nasal cavities of the patient. Thus, a column of air is trapped within the speaking valve and the tracheostomy tube acts as a buffer to resist movement of secretions that move up the tracheostomy tube and into the speaking valve. Such speaking valves while permitting patients to speak normally have serious drawbacks in connection with their use. First, the tracheostomy tube must operate with the cuff of the tracheostomy tube always completely deflated which otherwise creates a dangerous obstruction to exhaled air flow. Warning labels are often indicated in proximity to the patient's bedside and/or chart in order to monitor the balloon of the patient's cuffed tracheostomy tube. Another drawback is the case in which controlling the ventilation and gross aspiration is required, in order to prevent the tracheostomy tube cuff from being deflated. The speaking valves cannot be used in such cases since it would cause an obstruction to exhaled air flow and the patient would not be able to be safely ventilated. An additional drawback of speaking valves is for unconscious or comatose patients which are unable to speak in such states, and would require constant monitoring when such speaking valves are implemented with ventilation systems. Speaking valves are generally not suitable during extensive sleep patterns of patients, especially in unconscious or comatose patients. An additional complication is that any inadvertent re-inflation of the cuff can also occur with a foam-filled cuffed tracheostomy. The pilot line of a foam-filled cuffed tracheostomy tube must be plugged in to prevent the cuff from re-inflating. Therefore, the use of speaking valves can be hazardous when implemented with a foam-filled cuffed tracheostomy tube.

As described, there exists a need in the art for a ventilator tracheostomy adapter that not only permits optimal use of more advanced ventilator technologies implementing existing tracheostomies or use of an endotracheal tube (i.e. tube placed within the patient's trachea), but which additionally permit the continuous use of the ventilator with marked improvement in the speech of patients or simply, the ability to even speak, while reducing numerous potential complications and drawbacks of existing speaking valves. An advantage of such improved adapter designs is the possibility for refined calibration of continuous ventilator support in both the inspiratory and expiratory phases of respiration which leads to improved weaning of the patient from dependency on the ventilator for breathing as is described in greater detail below.

SUMMARY

Embodiments of the disclosure will become apparent from the following detailed description considered in conjunction with the accompanying drawings. It is to be understood, however, that the drawings are designed as an illustration only and not as a definition of the limits of this disclosure.

The disclosed technology is directed to a speaking valve adapter for assisting with speech or language expression during respiratory recovery of a human, the speaking valve adapter including a speaking valve port, the port being orthogonal to a first interface port, the first interface port adapted to support tracheostomy or endotracheal tubing, a second interface port adapted to support at least one of a suction tubing and a bronchoscopy tubing and a third interface port adapted to support a connection to a ventilator.

The speaking valve adapter is further directed to being used by the patient for introduction of at least one of sounds and words while connected to the ventilator. The first interface port further including a swivel adapter surrounding the opening channel to the first interface port. The swivel adapter may be further configured to have increased flexibility between the tracheostomy and the patient. The speaking valve adapter yet may further include the third interface port being further configured to include a swivel adapter surrounding the channel to the third interface port. The swivel adapter may further be configured to consist of material having increased flexibility, thereby increasing the user's range of movement while connected to the ventilator.

The speaking valve adapter may further include the second interface port comprising a plug for connection to an opening of the third interface port, thereby closing the opening to the third interface port. The third interface port may further comprise a plug for connection to an opening of the third interface port, thereby closing the opening to the third interface port. The speaking valve adapter may yet further comprise a plug for connection to an opening of the speaking valve adapter, thereby closing the opening to the speaking valve adapter. The tracheostomy may yet further include a cuff disposed along tubing of the tracheostomy. The tracheostomy may yet further include a cuff used during inflation or deflation of the cuff without risk of injury associated with connection to the ventilator.

The speaking valve adapter may be further configured to include a positive end expiratory pressure level being set on the ventilator while diverting air through the vocal cords during speech, thereby minimizing respiratory complications during speech. The speaking valve adapter may further include inspiration including simultaneous inspiration from outside atmospheric air at sea level pressure and pressure support from the ventilator. The speaking valve adapter may yet further include optimizing at least one ventilator parameter to reduce overall duration of ventilation and organ failure associated with connection to the ventilator.

The disclosed technology is yet further directed to a respiratory management system implementing a speaking valve adapter for assisting with speech or language expression during respiratory recovery of a human patient. The system including a ventilator configured to permit a human's lungs to deflate and rapidly inflate continuously to maintain the lungs nearly inflated, a speaking valve adapter, the adapter being configured to include a speaking valve port, the port being orthogonal to a first interface port, the first interface port adapted to support tracheostomy or endotracheal tubing, a second interface port adapted to support at least one of a suction tubing and a bronchoscopy tubing, and a third interface port adapted to support a connection to a ventilator.

Embodiments will become apparent from the following detailed description, which is to be read in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the following detailed description in conjunction with the accompanying drawings.

It is to be appreciated that elements in the figures are illustrated for simplicity and clarity. Common but well-understood elements, which may be useful or necessary in a commercially feasible embodiment, are not necessarily shown in order to facilitate a less hindered view of the illustrated embodiments.

DETAILED DESCRIPTION

It is noted that known speaking valves are generally designed to be in-line with the ventilator attachment. The disclosed technology overcomes the shortcomings resulting from this "in-line" design and introduces additional advantages to the recovery of the lungs during the weaning process using traditional as well as more current ventilator technologies. Additionally, there are added advantages in implementing the newer ventilator technologies in treatment centers, such advantages described in greater detail below. The present disclosure also permits simultaneous ventilation and suctioning via a suction/bronchoscopy port which is another advantage over known designs. Existing speaking valves can't be utilized if the tracheostomy cuff is inflated. Otherwise, patients face the risk of lung over-expansion and/or hyperinflation if attached to the ventilator while using such valves when the cuff is inflated. Air flows mainly to the outside when the cuff is deflated. However, when the cuff is inflated, all air egresses back into the endotracheal or tracheostomy tube, not only making speech impossible, but, causing a medically dangerous condition. Foam filled cuffed tracheostomy tubes also cannot be implemented with in-line speaking valve designs without the risk of lung overexpansion if the cuff re-inflates. Known speaking valves cannot be easily implemented with endotracheal tubes. Additionally, known speaking valves are not indicated for use with unconscious or comatose patients.

Figure 1:
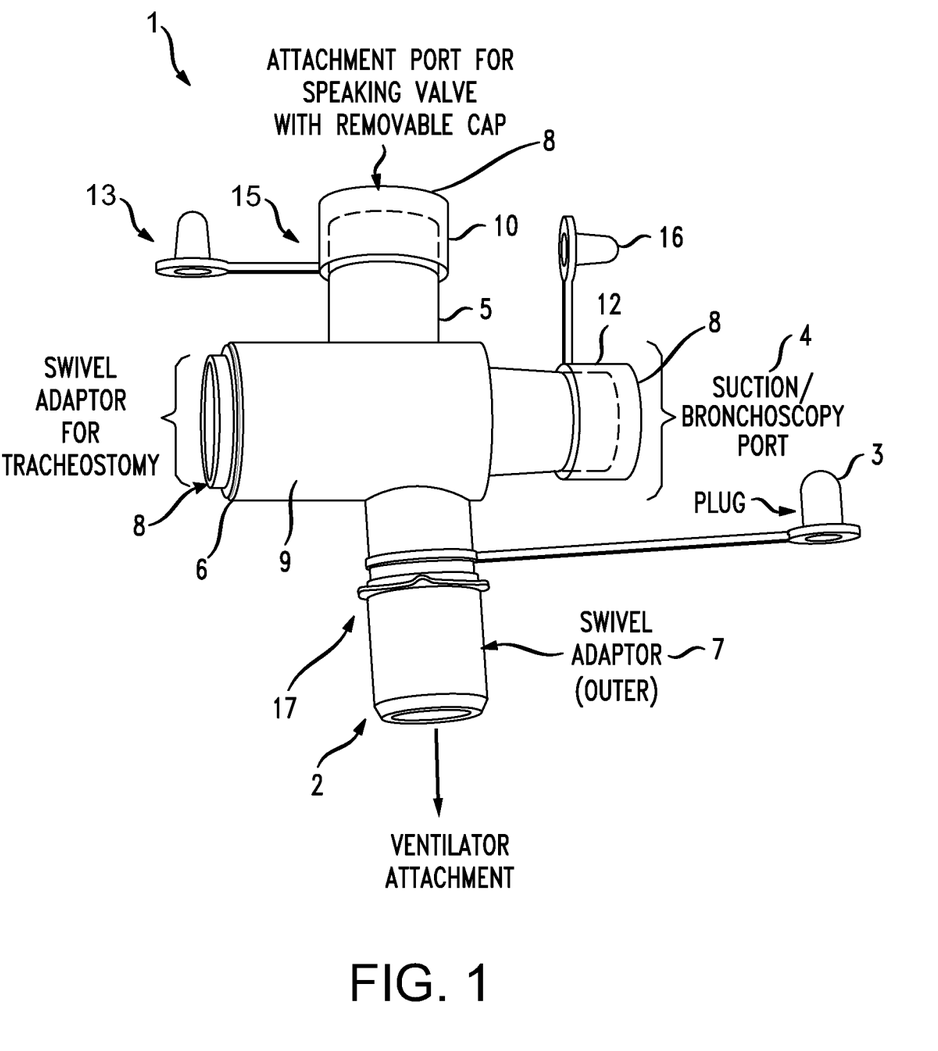
FIG. 1 is an illustration of a first preferred embodiment of the tracheostomy adapter for attachment to a ventilator.
Figure 4:
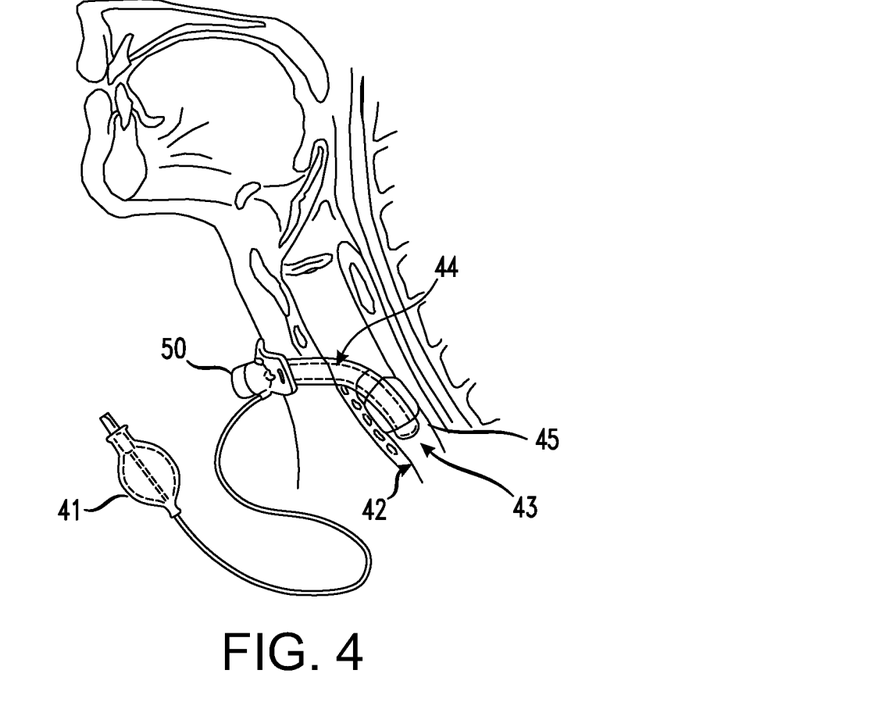
FIG. 4 is an illustration of a cuffed tracheostomy tube inserted in the trachea of a patient.
Figure 5:
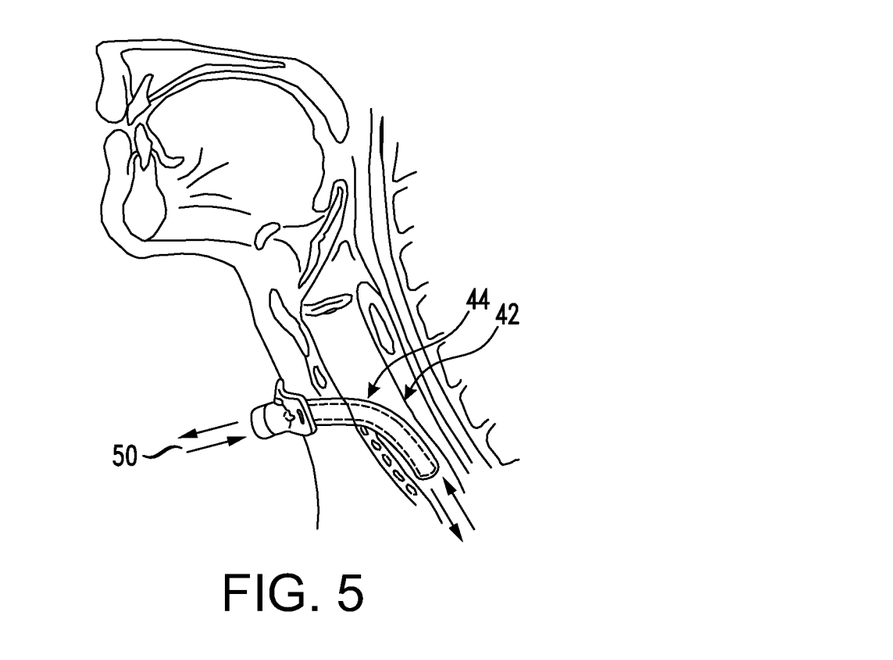
FIG. 5 is an illustration of an un-cuffed tracheostomy tube inserted in the trachea of a patient.
Figure 7:
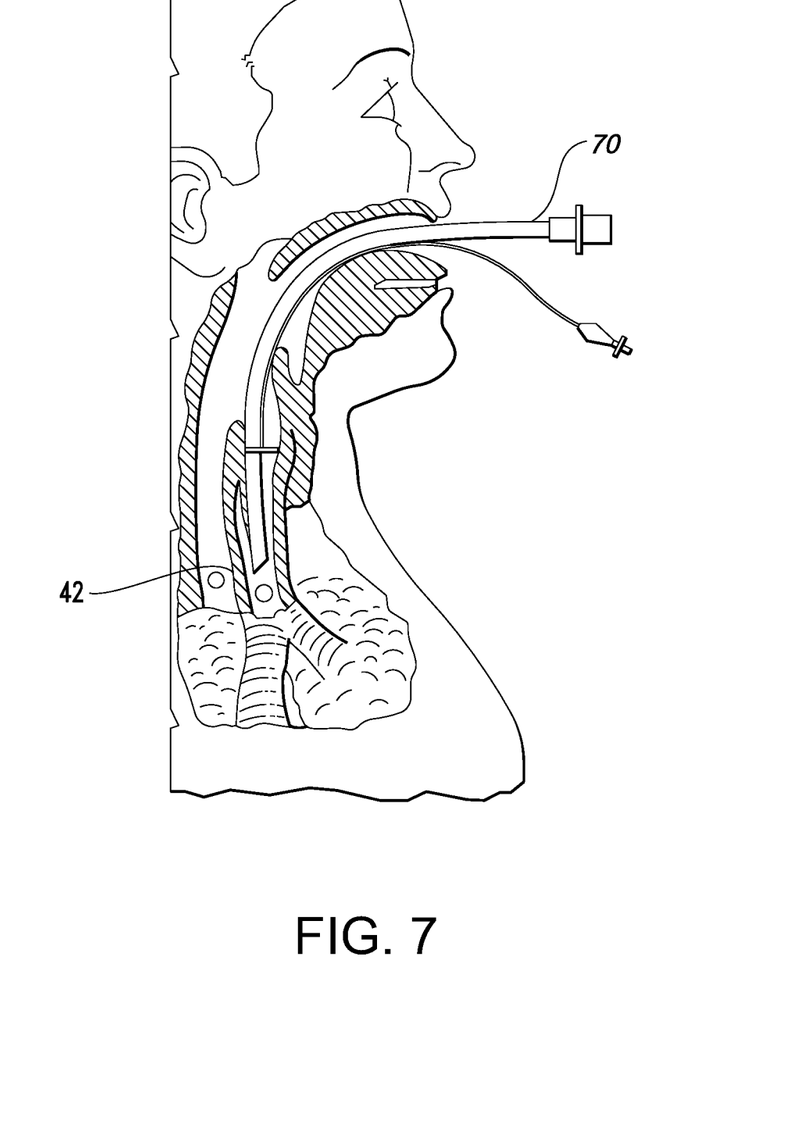
FIG. 7 is an illustration of an endotracheal tube as inserted in the trachea of a patient.

A speaking valve adapter (1) in accordance with the disclosed invention is shown in FIG. 1 as a preferred embodiment. The speaking valve adapter (1) may be attached to the external adapter (50) of a standard tracheostomy tube (44) as shown in FIGS. 4 and 5, respectively, whether the tracheostomy tube (44) is cuffed (41) or an un-cuffed model, for example, as shown in FIG. 5. The speaking valve adapter (1) in some embodiments or aspects, is attached to the external adapter of a standard endotracheal tube (70), as shown in FIG. 7.

The disclosed speaking valve adapter (1) in FIG. 1 permits attachment to either a tracheostomy or an endotracheal tube (70) at opening (8) of cylindrical tracheostomy port (9). A simple tracheostomy is generally inserted below the vocal cords of the patient. The airflow generally bypasses the vocal cords and thus, no speech is possible while connected to a tracheostomy if the balloon is inflated. When patients require ventilation for several weeks, a tracheostomy as shown in FIG. 4 and FIG. 5, provides better suited access to the trachea (42). The tracheostomy is a surgically created passage into the trachea (42). They are generally well-tolerated. However, many tracheostomies include a "cuff" (41) which is associated with risks as described in greater detail below.

Prior to tracheostomy, endotracheal intubation is customary. It includes the placement of a flexible plastic tube into the trachea (42) to maintain an open airway serving as a conduit for mechanical ventilation if indicated for the patient. Either method of facilitating connection to a ventilator may be indicated for a patient depending on the patient's condition. As shown in FIG. 1, the tracheostomy port (9) also includes a swivel adapter (6) that rotates about the cylindrical body of the tracheostomy port (9) at opening (8). The swivel adapter (6) connects likewise to either a tracheostomy tube (44) of FIG. 4 or an endotracheal tube (70) as shown in FIG. 7, for example. It is noted, that if an endotracheal tube (70) is inserted in the trachea (71) as shown in FIG. 7, the exhaled airflow of the patient goes back through the endotracheal tube (70) into the ventilator and thus, bypassing the vocal cords. No airflow can egress through the vocal cords to permit speech, if the cuff is inflated with either an endotracheal tube or tracheostomy. As already described, both endotracheal tube (70) and tracheostomy tube (44) are designed to have a cuff (41) or inflatable balloon, which is inflated and occupies the full diameter of the patient's internal tracheal diameter (43), as shown in FIG. 4. The cuff (41) in FIG. 4 is able to inflate or deflate with the same degree of air pressure under strictly controlled conditions which generally serves to prevent a pressure "sore" on the internal tissues of the tracheal wall (45) among other functions.

One of the advantages of the swivel feature of the adapter (1) of FIG. 1, is that the patient is able to move about comfortably while the tracheostomy tube is connected to the patient, which permits greater freedom of movement and flexibility for the tracheostomy tube itself as the patient moves about. The swivel adapter (6) will pivot or rotate about the opening (8) to the cylindrical body of the tracheostomy port (9) which increases flexibility in use for the patient as well as increases the patient's level of comfort. The swivel adapter (6) will also prevent any potential snagging or any other condition that would otherwise cause any physical obstruction of airflow via the tube due to constriction of movement of the valve. The swivel adapter (6) expands the patient's range of movement while connected thereto. The swivel adapter (6) in certain embodiments can be further configured to be manufactured of a flexible material such as for example, polyurethane, medical grade, resulting in even greater flexibility and/or ability to rotate while the patient is connected to the ventilator and the tracheostomy. This feature will increase the patient's level of comfort. The patient's ability to rest comfortably and relax while connected to the ventilator is also considered a significant factor that improves the overall recovery process. Hence, the swivel adapter (6) at the tracheostomy port (9) contributes to the patient's overall comfort, by increasing their freedom of movement.

The speaking valve adapter (1) also includes a cylindrical port (5) that supports the speaking valve (15). The speaking valve (15) may be removable in some embodiments or aspects, and/or include a removable cap (10) in certain embodiments. The removable cap (10) also permits covering the port by insertion of a plug (13) into the cylindrical port (5) opening (8) in the instance for example, when the patient does not want the assistance of the speaking valve (15). Thus, the removable cap (10) serves to cover the opening reducing incidence of contamination by any foreign substances.

The ventilator port (17) that is cylindrical and-supports attachment to the ventilator at opening (2), is enclosed by a outer swivel adapter (7) on its outer surface to permit greater freedom of movement for the patient while connected to the ventilator. There are also fewer occurrences of any obstruction of airflow with the outer swivel adapter (7) as it increases flexibility in use, and increases patient's level of comfort. In addition, the swivel adapter (7) decreases occurrences of any physical conditions in the attachment(s) to the ventilator that could form an impediment or obstruction of the airflow, thus impeding proper functioning of the ventilator. An incidental result of increasing the patient's flexibility of use is simultaneously increasing the patient's level of comfort and generally, the patient's breathing level is also generally enhanced.

Figure 8:
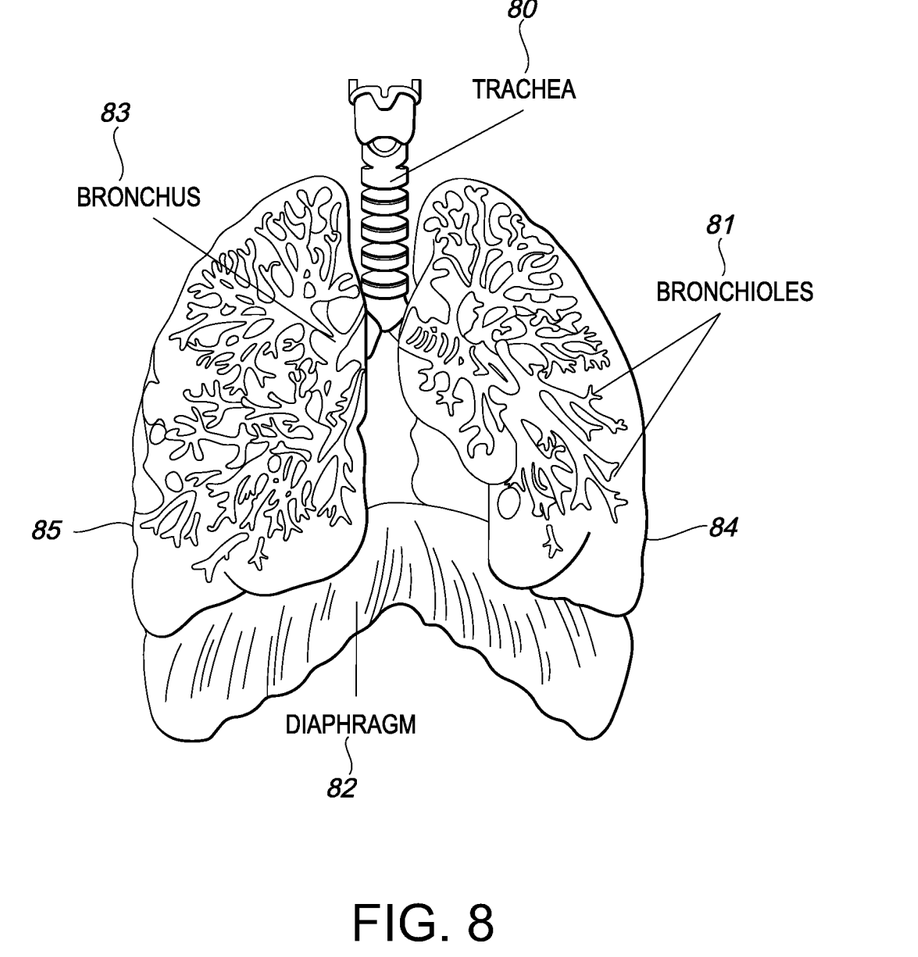
FIG. 8 is an illustration of the main respiratory airways of a human.

The suction/bronchoscopy port (4) is shown having an opening (8) for supporting attachment to a suction or bronchoscope. A bronchoscope is a long, narrow, fiberoptic, lighted viewing tube inserted through the nose or mouth. The physician can view as shown in FIG. 8, for example, in a non-intubated patient, the trachea (80), bronchi (83) (large airways to the lungs), and bronchioles (81) (smaller branches of the bronchi) in order to evaluate, diagnose and/or treat certain areas including performance of biopsies for examination of tissue, if medically indicated. The physician or health care provider may also remove secretions or foreign bodies and provide specialized treatments using such bronchoscopy procedures.

The suction/bronchoscopy port (4) of FIG. 1, includes a removable cap (12) with plug (16) attached to the cap. The removable cap (12) with plug (16) is used to close the opening (8) to the suction/bronchoscopy port (4) when not in use or connected to the suction or bronchoscope. An additional plug (3) found above the distal end of the swivel adapter (7) of the ventilator port attachment (2), may be used to close the opening (8) of the suction/bronchoscopy port (4) in the event for example, that the removable cap (12) is removed from the outer cylindrical surface of the suction/bronchoscopy port (4).

Figure 6:
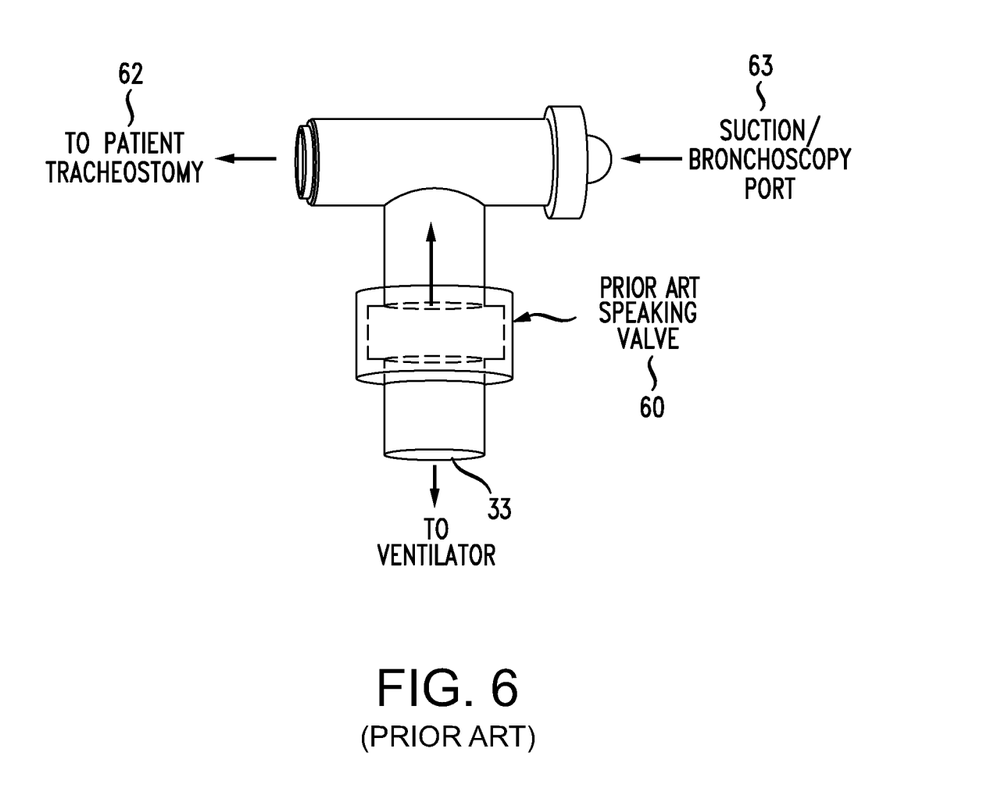
FIG. 6 is an illustration of an exemplary known tracheostomy valve with attachment port to a ventilator.

As described above, the disclosed speaking valve adapter (1) of FIG. 1 is designed to include a speaking valve (15) that is orthogonal with and directly connects to the tracheostomy port (9) rather than the prior art design of FIG. 6, in which the prior speaking valve (60) is arranged directly in-line and connects to the ventilator port (33) as shown in FIG. 6. The design of the disclosed embodiment is associated with improved results for both speaking ability and speech therapy during respiratory therapy. The disclosed embodiment is also associated with an improved weaning process for patients connected to newer ventilator technologies. These ventilators also more finely calibrated and are more tailored to a patient's unique needs. For example, certain of the ventilator technologies implements sensors that are neural-based. These sensors and ventilators work with a specialized nasal/oral gastric tube, while also sensing the electrical pulses sent from the brain to the diaphragm (82) as shown in FIG. 8. These sensors allow the ventilator to deliver pressure proportionally to the amount of diaphragmatic activity it measures. These newer ventilator technologies may use diaphragmatic electromyography to trigger ventilation in a more natural manner. This technology assists Respiratory Therapy personnel and physicians in adjusting ventilators to facilitate and mimic more natural breathing patterns for the patient in accordance with measured bodily responses and demands. The newer ventilators thereby generate a more normal breathing pattern for the patient who could not otherwise breathe normally and in sync with the ventilator. The disclosed speaking valve adapter (1) is designed to coordinate with these finely-tuned ventilator technologies that are more tailored towards the patient's level of functioning with greater accuracy while permitting adjustments in accordance with the patient's measured bodily functions. While conventional mechanical ventilators sense a patient's efforts by either a drop in airway pressure or a reversal in air flow, newer technologies evaluate electrical activity of the diaphragm and/or brain signals to couple the diaphragm and the ventilator's functioning near or actually instantaneously. This, in effect, synchronizes the patient's current breathing patterns with that of the ventilators.

The patient's expiratory cycle which is in tune with the patient's diaphragm cycle, may also be set by a practitioner. These features affect the ability to develop and initiate speech in the patient. More specifically, the expiratory back pressure created in ventilator tubing and during the ventilator's expiratory phase forming the patient's expiratory cycle may be set by the practitioner. Therefore, certain values such as PEEP or EPAP can be adjusted (as described in greater detail below). PEEP (positive end-expiratory pressure) is the pressure in the lungs above atmospheric pressure (the pressure outside of the body) that exists at the end of expiration. The two types of PEEP are extrinsic PEEP (PEEP applied by a ventilator) and intrinsic PEEP (PEEP caused by a non-complete exhalation). Pressure that is applied or increased during an inspiration is the pressure support in which the patient initiates every breath and the ventilator delivers support with the preset pressure value. EPAP (expiratory positive airway pressure) refers to the positive airway pressure being provided to the patient by the ventilator while the patient breathes out.

The above-described airflow paths do not create speech in and of itself, but by virtue of back pressure, can promote diversion of air flow through the vocal cords. Ventilator technologies also overcome the problems associated with older ventilators such as collapse of tiny air sacs at the end of the bronchiole as the cough reflex is absent and no natural, periodic or continuous positive and expiratory pressure being available naturally. In addition, current ventilator technologies also implement the monitoring of the diaphragm's activity, similar to monitoring an additional vital sign. This permits adjustments to the ventilator to facilitate breathing for each patient according to each person's unique bodily demands and functions thereby, mimicking or simulating a more normal breathing pattern. The newer ventilator technologies also are more geared towards improving the patients' recovery cycles and weaning the patients off the ventilators as soon as possible. The longer a patient is connected to a ventilator, the more risks for complications are present such as ventilator associated pneumonia and/or other injury related to the lungs and airways of a human.

Additionally, the newer ventilator technologies are associated with decreased duration of ventilator periods with developed weaning protocols having improved monitoring features while avoiding additional unnecessary sedation. Conventional ventilator technologies often rely on external indicators and since intubated patients are often unable to communicate their symptoms, etc. either due to sedation and/or lack of speaking abilities, it was often difficult for health care providers to interpret physiological changes indicated by monitors. In addition, these external indicators were oftentimes not accurate enough nor indicators of the patient's true state of condition and recovery. For example, symptoms such as rapid breathing, rapid heart rate, or agitation could be treated with sedating medications which could actually increase any respiratory failure. The streamlined and/or more current ventilators provide additional information to assist providers with determining whether further ventilator adjustments are required to modify ventilator support or whether the symptoms are arising from a different cause. Sensors allows these ventilators to deliver pressure proportional to the amount of diaphragmatic activity measured thereby allowing providers to adjust the ventilator according to the individual's bodily demands.

The disclosed technology utilizes these improved features associated with newer ventilator technologies while assisting health care providers with rehabilitating or improving speech during the weaning process from ventilators. While the newer ventilators are more optimal in weaning the patients from the ventilator, the use of the disclosed adapter is complimentary to these newer ventilators and assist with weaning the patients from dependence on the ventilators generally sooner than with conventional ventilators.

Known speaking valves are not indicated for improvement of the weaning process while permitting speech recovery efforts because of the already described drawbacks in such devices. As described, an example of a known speaking valve device is shown in FIG. 6. This valve (60) designed to be "in-line" with the ventilator port (33), attaches to the ventilator at such port. The attachments to the patient tracheostomy (62) and the suction/bronchoscopy port (63) are in-line to the speaking valve (60) and thus, the ventilator attachment port (63). This known device is associated with many of the already described disadvantages.

The process of weaning involves the gradual reduction of the amount of work that is performed by the ventilator as the patient's respiratory system gradually recovers or heals from their injury. Part of the recovery process for a patient is permitting the patient's own muscles to gradually function independently and be restored to the same level of functioning as prior to the patient's injury or respiratory illness, etc. The newer ventilators also have a wide variety of modes for ventilation to suit the unique nature of the patient's respiratory injury while permitting weaning sooner. Ventilators include complex pressure modalities which offer diverse ways to control the air pressure and ventilator support whether the patient is assisted with inhaling or exhaling. Some of the various modalities of ventilators include IMV (intermittent mandatory ventilation), SIMV (synchronized intermittent mandatory ventilation), pressure control, airway pressure release, assist control, volume control, volume assist, bi-level, BIPAP (bi-level positive airway pressure), CPAP (continuous positive airway pressure), etc.

Some of the recent additions are pressure control ventilation, pressure support ventilation, and synchronous intermittent mandatory ventilation (SIMV). SIMV is designed to provide assured rates and tidal volumes not competing with the patient's own spontaneous efforts. SIMV can synchronize the patient's breathing with ventilator operations thus, reducing the patient's tendency to fight the ventilator and the need for sedation or other narcotics for the patient to better tolerate mechanical ventilation. Synchronizing the patient's efforts with the ventilator provides significant clinical advantages than previous conventional CMV (continuous mandatory ventilation). Associated risks associated with typical mechanical ventilators include for example, barotrauma, ventilator-associated lung injury, and/or atrophy of diaphragm related muscles.

FIG. 8 is an illustration of the human main airways including trachea (80), bronchus (83), bronchioles (81) and diaphragm (82) located below the right (85) and left (84) lungs. It is the diaphragm (82) and related muscles which are important to develop strength to aid in the weaning process from the ventilator.

Figure 2:
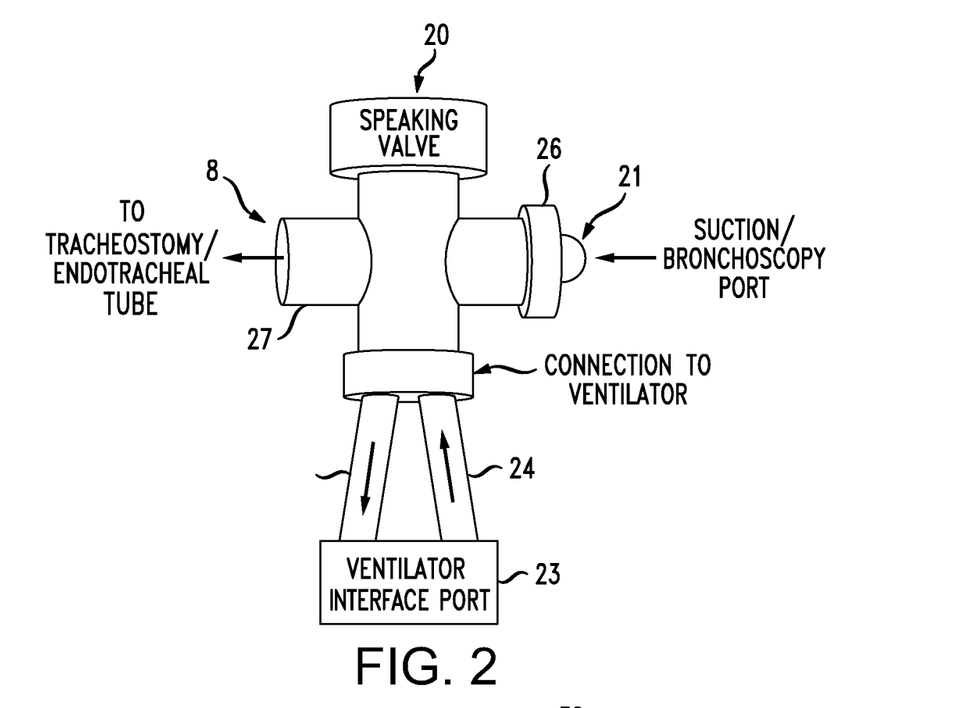
FIG. 2 is an illustration of a second embodiment of the tracheostomy adapter for attachment to a ventilator.

FIG. 2 is an illustration of an embodiment of the speaking valve adapter that includes an opening (8) for connection of or attachment of the tracheostomy/endotracheal port (27) to either a tracheostomy tube (44) or an endotracheal tube (70). The suction/bronchoscopy port (21) connects optionally with removable cap (26) to a suction and/or bronchoscopy attachment. The ventilator interface port (23) includes two cylindrical tubes that are disposed in a skewed fashion and support one-directional airflow associated with either the expiration of air (25) from the human's lungs and/or the inhalation of air (24) into the human's lungs.

Figure 3:
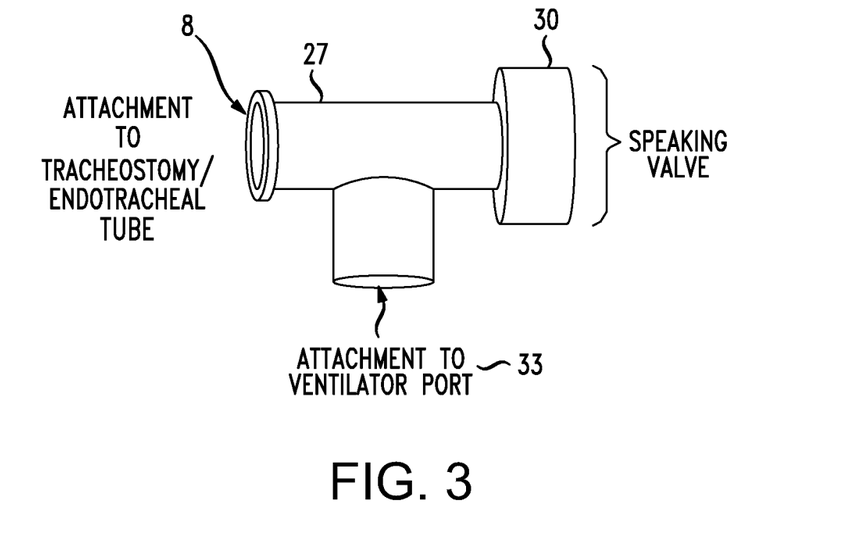
FIG. 3 is an illustration of a third embodiment of the tracheostomy adapter for attachment to a ventilator.

FIG. 3 is an illustration of an embodiment of the adapter with an opening (8) for supporting connection of or attachment of the tracheostomy/endotracheal port (27) to either a tracheostomy tube (44) or an endotracheal tube (70). The ventilator port (33) supporting attachment to the ventilator is orthogonal relative to the speaking valve (30).

It is noted that with each of the shown embodiments of the invention, the ventilator may ventilate the patient whether the tracheostomy cuff is inflated or not. As with any speaking valve, the effect on the expiratory phase while speech actually occurs, is noted by the back pressure being presented by the ventilator to the air column in the tracheostomy during the expiratory cycle and further, the speaking valve critically deflecting or re-directing air back up the vocal cords. This feature could also be accomplished with known "in line" speaking valves as shown in FIG. 6, however, the cuff (41) on the patient must be mandatorily deflated or otherwise, would result in serious complications to the patient. If the cuff (41) had to be re-inflated due to for example, progressive hypercapnia (hypoventilation) or emergent changes in the patient's status, the speaking valve of FIG. 6 would have to be removed and the ventilator reset which is a significant drawback in the use of these "in-line" speaking valves.

In other embodiments or aspects during implementation of the disclosed speaking valve adapter shown in either FIG. 1, 2 or 3, the patient's cuff (41) may be inflated without changing the speaking functionality and without disruption of the connection to the ventilator. Since the speaking valve is orthogonal relative to the cylindrical tracheostomy port (9), (shown in FIGS. 1 and 2) and orthogonal relative to the ventilator port (33) (as shown for example, in FIG. 3), any functionality is thereby preserved while even making rapid ventilator adjustments to suit the patient's current breathing requirements and vital signs. An additional advantage of the disclosed embodiments is that the speaking valve adapter allows for further refined calibration of continuous ventilator support in both the inspiratory and expiratory phases of respiration which is critical for the weaning process. When applying various features of newer ventilation features, it is noted that known speaking valves have been opened during inspiration phase despite any applied positive pressure ventilation. Therefore, a patient during inhalation would or could derive part of an inhaled breath from the outside atmosphere separate from the ventilator while also being supplied with additional pressure support from the ventilator. During expiration, it was found that the known valves closed and the ventilator was also able to register an end expiratory pressure level.

During the weaning process, air can be inhaled from non-ventilator produced air pressure and a fractional amount of air may travel in through the speaking valve. This amount of air can be gauged by the amount of work expended by the ventilator or (based on the already described indicators available in newer ventilator technologies) as compared to the patient breathing levels.

It is also noted that newer ventilator technologies also incorporate carbon dioxide sensors which can determine exhaled carbon dioxide levels by allowing back pressure air to be measured during the expiratory phase of respiration. During the expiratory phase, the speaking valve is closed and back pressure in the ventilator deflects air back up into the tracheostomy (with the cuff being deflated) and is expelled through the vocal cords of the patient. An ideal amount of PEEP/EPAP can also be optimized for prevention of atelectasis (collapse of the lung tissue and/or lung). This additional control, in effect enhances the use of the speaking valve (15), (20) or (30) by further manipulating the expiratory phase of the patient's breathing.

Another advantage of using the adapter in accordance with the disclosed embodiments, is the improved synchrony between the ventilators and the patient as soon as neural inspiration commences. The level of support and assistance that will be provided to the patient during inspiration is now determinable by the patient's own respiratory demands as now measurable using the newer ventilator technologies. This is also true for the cycling-off phase whereby the ventilator cycles off inspiration once alerted to the onset of neural expiration. Signals implemented in newer ventilator technologies are able to sustain synchrony between the patient and the ventilator. An incidental benefit of improved synchrony between patient and ventilator is improved ability to speak while connected to the ventilator. Another incidental benefit is protection of the patient's lungs and overall recovery process since the newer ventilators prevent over or under assistance of the patient which could otherwise, significantly hinder the patient's recovery process. For example, over assistance can prevent restoration of functioning and strength of diaphragm muscle(s).

Figure 9:
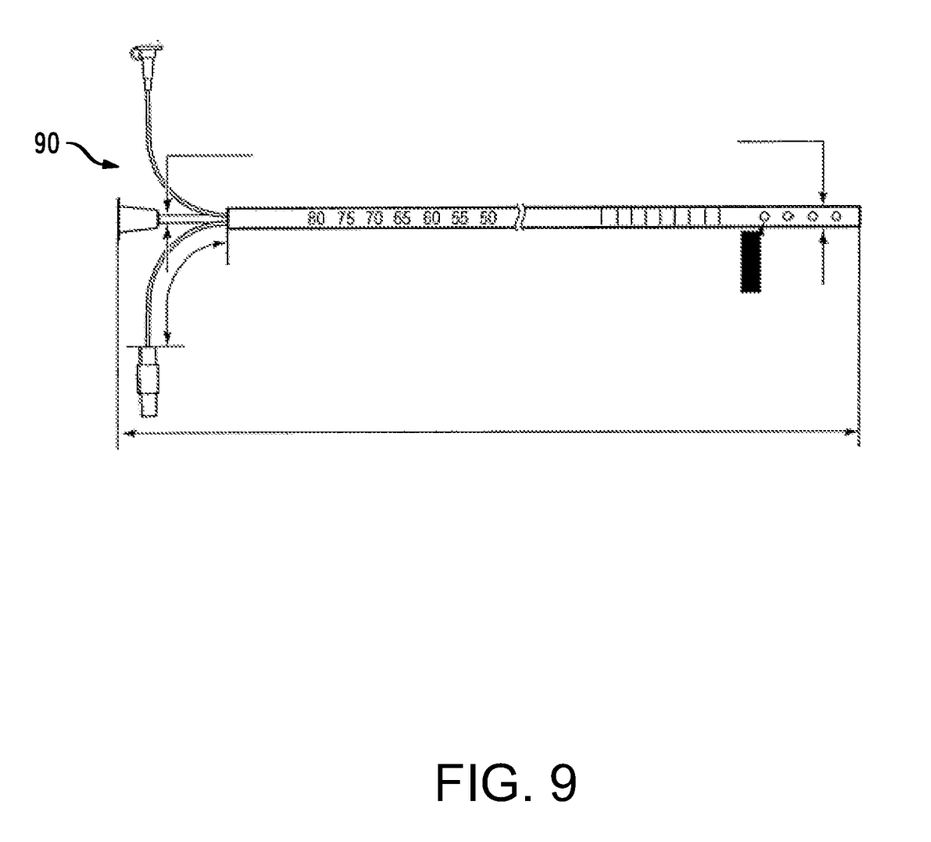
FIG. 9 is an illustration of an example Edi catheter.

Generally, the respiratory muscles and the ventilator will be driven by the same signals which essentially match the patient's neural demands. The newer ventilator technologies measure the electrical activity of the diaphragm using known methods such as insertion of an Edi catheter. An example Edi catheter (90) is shown in FIG. 9. The Edi catheter (90) includes at least a feeding lumen connector type with universal funnel connector and an auxiliary lumen connect with reducer and plug. The Edi catheter (90) detects electrical activity of the diaphragm and includes a barium strip for x-ray identification. They are available in different proportions for a full range of patients including neonates, pediatrics and adults. The Edi catheter (90) also works as a normal naso gastric feeding tube. Such signals can be used to assess respiratory drive, volume requirements, and the effects of ventilator settings on the particular patient. An esophageal ECG (electrocardiogram) can also be implemented during ventilator management to measure among other factors, decreases or increases in pressure as well as respiratory rates.

The result of such additional neurally-based detection and other ventilator management measures minimizes patient discomfort and agitation, promoting spontaneous breathing and in effect, reducing sedation when stable breathing conditions are met by and for the patient. As described, the current ventilators generally provide additional information for ventilator management and respiratory care such as respiratory drive, volume requirements, greater effect of tailored ventilator settings and greater indicators for sedation and weaning. Health care providers can now take advantage of these added features while implementing the speaking valve in accordance with the disclosed embodiments. Improved results include the patient's ability to speak sooner and more comfortably while attached to the ventilators including effectively improving the overall weaning process.

Figure 10:
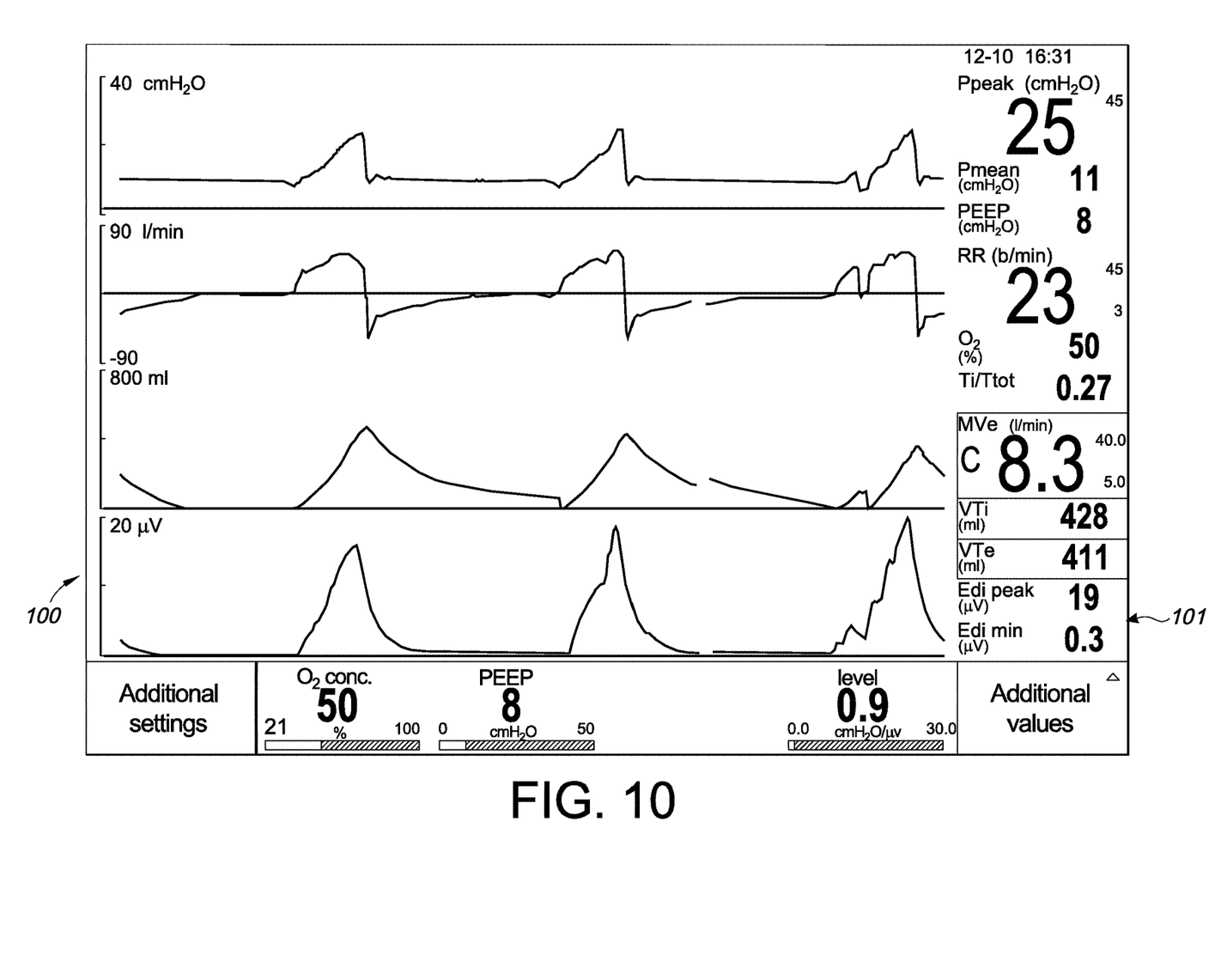
FIG. 10 is an illustration of an example ECG and Edi signal reading including PEEP, Oxygen, and additional levels.

FIG. 10 is an example ECG and Edi signal reading output including PEEP, oxygen, and additional output levels. The Edi signal reading having certain amplitude values measured in V is shown at signal output (100) with resultant Edi peak and min values shown at (101). These signal readings are all implemented in newer ventilator technologies to assist with adapting the patient to his or her optimal breathing levels while permitting weaning and speech recovery efforts. In ventilators implementing neuro-ventilatory coupling, the technology is based on the principle that the phrenic nerve is known to cause diaphragm excitation and stimulates many of the muscles of the upper thoracic cage including the diaphragm. The neural control of respiration originates in the respiratory center and these signals are transmitted through the phrenic nerve to excite the diaphragm. Therefore, these neural-based ventilators are controlled directly by the patient's own neural control of breathing.

Certain levels are able to be observed such as diaphragm excitation, diaphragm contraction, chest wall and lung expansion, airway pressure, flow and volume. The newer ventilators implement certain patient controls using neural triggers (including initiation of breath, inspiratory time, rate, peak pressure and termination of breath). These signals are monitored using bipolar electrodes for example, using electrodes mounted in the Edi catheter (90). Various ranges of models and sizes of these catheters are available which ensures optimized signal quality across all patient categories and conditions. It is further indicated for the insertion of the Edi catheters, that they are positioned properly and to a measured depth in the patient cavity which an esophageal ECG can confirm. A prominent P-wave is generally visible in the uppermost channel with a decline of P-wave amplitudes in the lower leads, once the catheter is properly positioned.

These neural-ventilator controls can include FiO2, PEEP, other ventilator specific levels such as a neurally adjusted ventilator assist level, Apnea time (minimum rate) and peak inspiratory pressure alarm. Synchrony is achieved observing factors such as initiation of breath, size of breath and termination of breath. These ventilators set values such as a neurally-adjusted ventilator assist level by converting for example, the Edi signal into a pressure level. The higher the neurally adjusted ventilator assist level, the ventilator must perform additional work. The goal of unloading the work of breathing from the patient to the ventilator without over assisting the patient is more successful with these neural-based ventilators. In parallel is the greater level of success with speech therapy efforts and the mere ability to speak using the speaking valve of FIG. 1, 2, or 3, while connected to such ventilators.

Non-invasive electrical impedance tomographic (EIT) monitors may also be implemented with the speaking valve adapter of FIG. 1, 2 or 3, and ventilators, in order to monitor and determine ventilation reacted impedance changes that occur in a thoracic cross-section. Such monitors enable the assessment of regional ventilation distribution as well as short-term changes in end-expiratory lung volumes. These monitors help assess conditions associated with ventilator use such as atelectasis (lung failure), over-inflation, air trapping, pleural effusion (excess fluid between the two membranes that cover the lungs) or pneumothorax (a buildup of air in the space between the lung and the chest wall, i.e., pleural space). This information may be displayed as images, waveforms or parameters to trend display of changes in end-expiratory lung volume.

Managed ventilator and speech recovery is enhanced when implementing systems using neural-ventilator type models coupled with the speaking valve adapter of the disclosed technology to assist the patient with weaning and speech during respiratory recovery and may include the use of additional monitors such as for example, EIT type monitors, for effective ventilator management.

Figure 11:
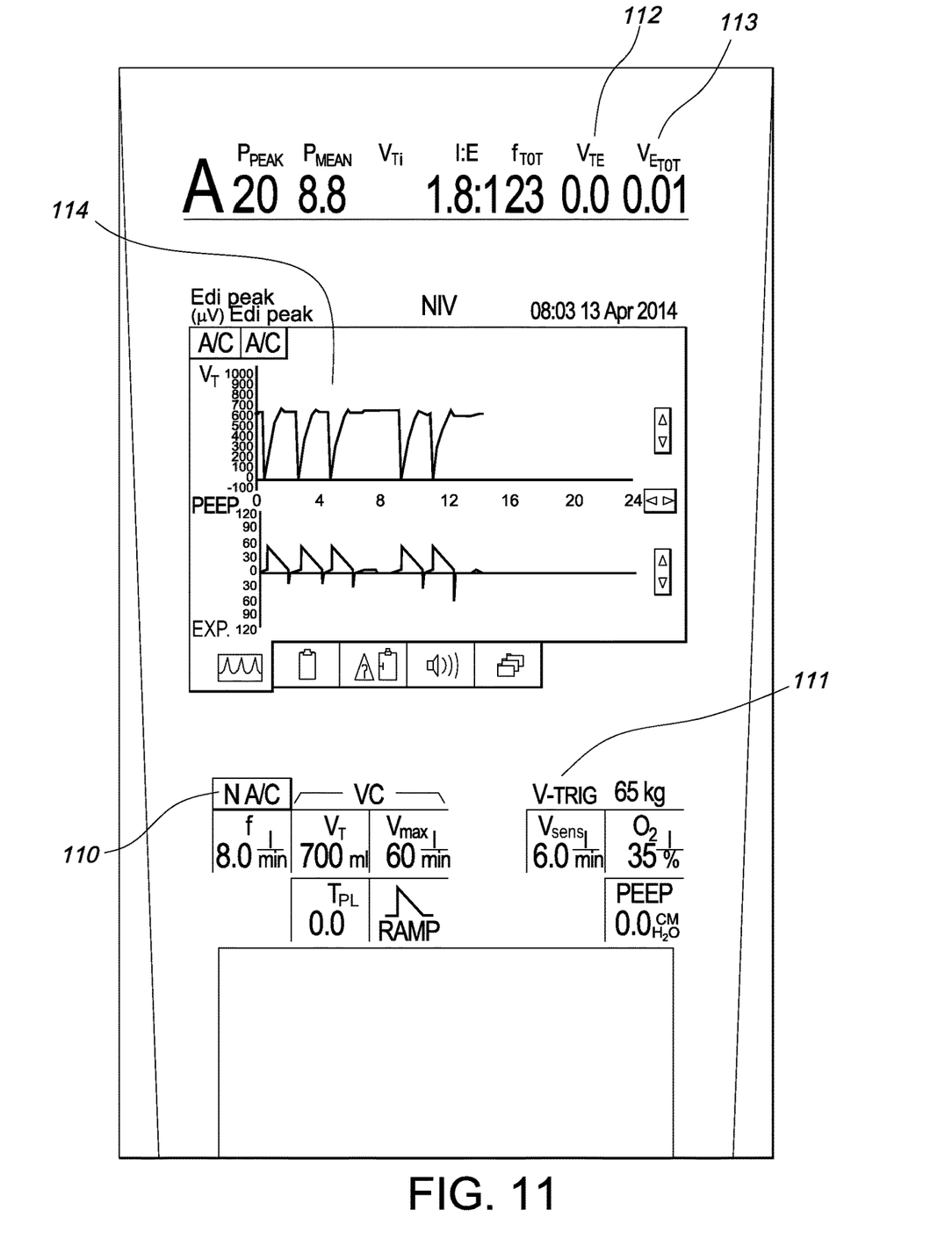
FIG. 11 is an illustration of an example prototype ventilator implemented with the tracheostomy adapter of the present invention.

FIG. 11 shows an example of ventilator settings set to optimize the implementation of the above-described speaking valve adapter in accordance with the disclosed respiratory management system. The ventilator settings could be used with a tracheostomy with the balloon cuff also being deflated. In a normal ventilator mode, when the balloon is inadvertently deflated, experiencing leaks or is otherwise ruptured, the ventilator does not sense any return volume. Consequently, the ventilator will constantly alarm and will auto-cycle ventilate the patient over 40-50 times. The settings displayed include N A/C of 8.0 (110) NIV (non-invasive ventilation) with a V-TRIG (111) of 6. With these type of settings for the ventilator, an alarm cycling condition is overcome. In the top bar, it is noted that $V_{TE}$(112) is 0 and $V_{ETOT}$ (113) is 0.01 but, reflect the timing of the respiratory cycle at the moment shown in FIG. 11. In such case, no air is coming or being diverted back, but rather is directed through the vocal cords by the speaking valve, which thereby permits speech of the patient while connected thereto during such respiratory cycle(s).

NIV refers to non-invasive ventilation which is a newer advanced function of the newer generation of ventilators. The wave form (114) demonstrates the ability of the ventilator to keep the lungs inflated despite the open circuit and the balloon being deflated. This in effect, creates a pattern that is similar to airway pressure release, i.e. APRV. The lung deflates and then rapidly inflates again rather than inflates, deflates and pauses in a near empty FVC (forced vital capacity) at FRC (functional residual capacity) rather than full inflation at near TLD (Total Lung Capacity) with attention to avoiding over-inflation as is seen here utilizing the settings as shown in FIG. 11. While these settings are inherent with all of the newer ventilators, they are not present in older generation models.

Prior art utilizing speaking valves have placed them in line with the ventilator circuit. The intent with most speaking valves is to place them on the tracheostomy. Placing them by the in-line arrangement has multiple hazards, which are overcome with the current disclosed embodiments. Using a speaking valve orthogonal to the ventilator with a cuff, ongoing ventilation remains possible with suctioning possible as needed but, in effect improving the overall ability for the patient to produce speech in a safe and more effective manner. When the patient makes an effort, not displayed here, but seen on manikin testing, the speaking valve still has air ingressing during inspiration despite ventilator support. Thus, it is a patient determined function balanced against ventilator support to determine just how much outside air versus ventilator support is being used by the patient. As less ventilator support is used, more outside ambient air is used as the lung heals. This healing process cannot be predicted or forced. The healing process is also dictated by the healing of an organ at whatever pace is foreordained by the original nature of the pulmonary injury and/or the respiratory condition.

Although preferred embodiments of the present invention have been described herein with reference to the accompanying drawings, it is to be understood that the invention is not limited to those precise embodiments and that various other changes and modifications may be affected herein by one skilled in the art without departing from the scope or spirit of the invention, and that it is intended to claim all such changes and modifications that fall within the scope of the invention.

The illustrations of embodiments described herein are intended to provide a general understanding of the structure of various embodiments, and they are not intended to serve as a complete description of all the elements and features of the speaking valve adapter and respiratory management systems imploring ventilators and the disclosed adapter, that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "embodiment" merely for convenience and without intending to voluntarily limit the scope of this application to any single embodiment or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 31 C.F.R. § 1.12(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Although specific example embodiments have been described, it will be evident that various modifications and changes may be made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate example embodiment.

The invention claimed is:

1. A speaking valve adapter for assisting with speech or language expression during respiratory recovery of a human by enabling vocal cord sounds produced on exhalation, the speaking valve adapter including:
   a speaking valve port, the speaking valve port being orthogonal to a first interface port, the first interface port configured to attach to tracheostomy tubing that comprises an un-cuffed or cuffed arrangement which enables balancing of atmospheric air with ventilator air;
   a second interface port adapted to support at least one of a suction tubing and a bronchoscopy tubing; and
   a third interface port adapted to support a connection to a ventilator, the speaking valve adapter enabling vocal cord sounds produced on exhalation during the respiratory recovery of the human; thereby improving speaking ability and speech therapy during respiratory therapy.

2. The speaking valve adapter of claim 1, wherein the speaking valve adapter is used by the human for introduction of at least one of sounds and words while connected to the ventilator.

3. The speaking valve adapter of claim 2, wherein a positive end expiratory pressure level may be set on the ventilator to allow diverting air through the vocal cords for speech, thereby minimizing respiratory complications during any speech.

4. The speaking valve adapter of claim 1, wherein the first interface port further comprises a swivel adapter surrounding the opening channel to the first interface port.

5. The speaking valve adapter of claim 4, wherein the swivel adapter is further configured to have increased flexibility between the tracheostomy tubing and the human.

6. The speaking valve adapter of claim 4, wherein the swivel adapter is further configured to consist of material having increased flexibility, thereby increasing a range of movement of the human while connected to the ventilator.

7. The speaking valve adapter of claim 1, wherein the third interface port is further configured to include a swivel adapter surrounding the channel to the third interface port.

8. The speaking valve adapter of claim 7, wherein the swivel adapter is further configured to consist of material having increased flexibility, thereby increasing a range of movement of the human while connected to the ventilator.

9. The speaking valve adapter of claim 1, wherein the second interface port further comprises a plug for connection to an opening of the second interface port, thereby closing the opening to the second interface port.

10. The speaking valve adapter of claim 1, wherein the third interface port further comprises a removable plug for connection to an opening of the third interface port, thereby closing the opening to the third interface port.

11. The speaking valve adapter of claim 1, wherein the speaking valve adapter further comprises a plug for connection to an opening of the speaking valve adapter, thereby closing the opening to the speaking valve adapter.

12. The speaking valve adapter of claim 1, wherein the tracheostomy tubing further comprises a cuff being used during inflation or deflation of the cuff without risk of lung or vocal cord injury while connected to the ventilator.

13. The speaking valve adapter of claim 1, wherein inspiration includes simultaneous inspiration of air from outside atmospheric air at sea level pressure and air by pressure support from the ventilator.

14. The speaking valve adapter of claim 1, wherein at least one ventilator parameter may be further configured to reduce overall duration of ventilation and reducing respiratory failure.

15. The speaking valve adapter of claim 14, wherein optimizing at least one ventilator parameter further includes optimizing ventilator management of the human, thereby reducing the overall duration of ventilation and reducing respiratory failure.

16. The speaking valve adapter of claim 1, wherein the first interface port is further adapted to attach to endotracheal tubing.

17. A respiratory management system for assisting with speech or language expression during respiratory recovery of a human by enabling vocal cord sounds produced on exhalation, the system including:
  a ventilator having settings configured to permit human lungs to deflate and rapidly inflate continuously to maintain the lungs nearly inflated;
  a speaking valve adapter, the speaking valve adapter being configured to include:
    a speaking valve port, the speaking valve port being orthogonal to a first interface port, the first interface port configured to attach to tracheostomy tubing that comprises an un-cuffed or cuffed arrangement which enables balancing of atmospheric air with ventilator air;
    a second interface port adapted to support at least one of a suction tubing and a bronchoscopy tubing; and
    a third interface port adapted to support a connection to a ventilator the speaking valve adapter enabling vocal cord sounds produced on exhalation during the respiratory recovery of the human; thereby improving speaking ability and speech therapy during respiratory therapy.

18. The respiratory management system of claim 17, wherein the speaking valve adapter is used to enable creation of at least one of sounds and words while connected to the ventilator.

19. The respiratory management system of claim 17, wherein the first interface port further comprises a swivel adapter surrounding the opening channel to the first interface port.

20. The respiratory management system of claim 17, wherein the ventilator further comprises ventilator settings which are configurable to assist the human with speech expression during the respiratory recovery of the human.

21. The respiratory management system of claim 20, wherein the ventilator settings include at least one of N A/C and V-TRIG parameters.

22. The respiratory management system of claim 17, wherein the first interface port is further adapted to attach to endotracheal tubing.

* * * * *

UNITED STATES PATENT AND TRADEMARK OFFICE
CERTIFICATE OF CORRECTION

PATENT NO. : 10,532,171 B2
APPLICATION NO. : 15/119225
DATED : January 14, 2020
INVENTOR(S) : Frank H. Arlinghaus, Jr.

It is certified that error appears in the above-identified patent and that said Letters Patent is hereby corrected as shown below:

In the Specification

Column 11, Line 24:
Now reads: "measured in V"
Should read: -- measured in µV --

Signed and Sealed this
Twenty-second Day of September, 2020

Andrei Iancu
*Director of the United States Patent and Trademark Office*